(12) United States Patent
Hovel et al.

(10) Patent No.: US 10,352,084 B2
(45) Date of Patent: Jul. 16, 2019

(54) SYSTEM AND METHOD FOR MONITORING A CABIN OF A MACHINE

(71) Applicant: Caterpillar Inc., Peoria, IL (US)

(72) Inventors: Douglas John Hovel, Lincoln, IL (US);
Daren Robert Carr, Normal, IL (US);
Erick Alan Njos, Sahuarita, AZ (US);
Daniel Alan Spurgeon, Washington, IL (US); Micheal David Valerio, Morton, IL (US)

(73) Assignee: Caterpillar Inc., Deerfield, IL (US)

( * ) Notice: Subject to any disclaimer, the term of this patent is extended or adjusted under 35 U.S.C. 154(b) by 189 days.

(21) Appl. No.: 15/651,405

(22) Filed: Jul. 17, 2017

(65) Prior Publication Data

US 2019/0017312 A1    Jan. 17, 2019

(51) Int. Cl.
*E05F 15/70*    (2015.01)
*G01N 33/00*    (2006.01)

(52) U.S. Cl.
CPC .......... *E05F 15/70* (2015.01); *G01N 33/004* (2013.01); *E05Y 2900/518* (2013.01); *E05Y 2900/531* (2013.01); *E05Y 2900/55* (2013.01)

(58) Field of Classification Search
USPC ........................................................ 701/49
See application file for complete search history.

(56) References Cited

U.S. PATENT DOCUMENTS

| | | | |
|---|---|---|---|
| 5,166,586 A | 11/1992 | Yaguchi | |
| 6,452,510 B1 | 9/2002 | Zysko | |
| 6,758,739 B1 * | 7/2004 | Sangwan | B60H 1/008 454/139 |
| 6,768,423 B2 | 7/2004 | Doescher et al. | |
| 6,988,670 B2 | 1/2006 | Keen et al. | |
| 9,656,534 B2 | 5/2017 | Wade et al. | |
| 2009/0069984 A1 * | 3/2009 | Turner | E05F 15/71 701/49 |
| 2011/0088637 A1 * | 4/2011 | Hirasawa | B60K 11/04 123/41.31 |
| 2014/0339001 A1 * | 11/2014 | Tokiwa | B60H 1/00378 180/89.12 |
| 2015/0032266 A1 * | 1/2015 | Weast | B60H 1/008 700/276 |
| 2016/0103111 A1 * | 4/2016 | Griffin | G01N 33/0067 73/25.01 |
| 2019/0017312 A1 * | 1/2019 | Hovel | E05F 15/70 |

FOREIGN PATENT DOCUMENTS

| | | |
|---|---|---|
| CN | 103410399 | 11/2013 |
| CN | 205149457 | 4/2016 |
| WO | WO2011145781 | 11/2011 |
| WO | WO2016167690 | 10/2016 |

* cited by examiner

*Primary Examiner* — Tyler D Paige

(57) ABSTRACT

A system and method for monitoring a cabin of machine is provided. The system includes an operator presence sensor, a cabin pressure sensor, a door sensor, and a carbon dioxide sensor configured to generate the first output signal, the second output signal, the third output signal and the fourth output signal respectively. The system includes a controller configured to selectively process at least one of the first output signal, the second output signal, the third output signal or the fourth output signal. The controller is further configured to control one or more conditions inside the cabin based on the selective processing of the at least one of the first output signal, the second output signal, the third output signal or the fourth output signal.

20 Claims, 3 Drawing Sheets

SYSTEM AND METHOD FOR MONITORING A CABIN OF A MACHINE

TECHNICAL FIELD

The present disclosure relates to cabins for operators of machines. More particularly, the present disclosure relates to system and method for monitoring a cabin of a machine.

BACKGROUND

Earth-moving machines, such as cable shovels, excavators, wheel loaders, and haul trucks often operate in harsh conditions. These conditions can include extreme temperatures and dirty, dusty environments. In order to keep operators of these machines comfortable and to improve productivity of the machines, one or more parameters associated with the cabins of these machines are usually controlled. For example, the cabins can be pressurized to keep dust and debris out of the cabins, and the temperature of the cabins can be reduced via air conditioning.

Heating/ventilation/air conditioning (HVAC) systems of the machine play a significant role in maintaining the air quality inside the cabin. HVAC systems direct airflow from one or more inlet points, through heater cores and/or evaporator cores and onto a number of outlets. The airflow through the HVAC system is generally controlled by airflow doors to open, close or blend the air through various passages through the HVAC system. Cabins are provided with a user interface by which the operator controls the airflow.

A typical HVAC system comprises a variety of air temperature sensors, pressure sensors, humidity sensors, pollutant sensors, air filter sensors (both pressure or infrared) and positional sensors. Any abnormality in sensor data is signaled to the operator via the user interface. These sensors are individually connected to the HVAC system or other control systems. Thus, the operator needs to review the output of all these sensors separately in order to diagnose the problem and come up with solutions. Further, some sensors generate false alarms as these are not optimized for use in different types of operating environments and/or different machines.

The present disclosure is directed to solving one or more of the problems set forth above and/or other problems of the prior art.

SUMMARY

In an aspect of the present disclosure, a system for controlling one or more conditions inside a cabin of a machine is provided. The system comprises an operator presence sensor for detecting presence of an operator inside the cabin, and generate a first output signal. The system comprises a cabin pressure sensor for determining a pressure inside the cabin, and generate a second output signal. The system comprises a door sensor for detecting whether doors of the cabin are open, and generate a third output signal. The system comprises a carbon dioxide sensor for determining a level of carbon dioxide inside the cabin, and generate a fourth output signal. The system comprises a controller communicably coupled to the operator presence sensor, the cabin pressure sensor, the door sensor, and the carbon dioxide sensor. The controller is configured to receive the first output signal, the second output signal, the third output signal, and the fourth output signal. The controller is configured to selectively process at least one of the first output signal, the second output signal, the third output signal, or the fourth output signal based on one or more rules. The controller is further configured to control the one or more conditions inside the cabin based on the selective processing of the at least one of the first output signal, the second output signal, the third output signal, and the fourth output signal.

In another aspect of the present disclosure, a method for controlling one or more conditions inside a cabin of a machine is provided. The method includes detecting, by an operator presence sensor, presence of an operator inside the cabin, and generating, by the operator presence sensor, a first output signal. The method includes determining, by a cabin pressure sensor, a pressure inside the cabin, and generating, by the cabin pressure sensor, a second output signal. The method includes detecting, by a door sensor, whether doors of the cabin are open, and generating, by the door sensor, a third output signal. The method includes determining, by a carbon dioxide sensor, a level of carbon dioxide inside the cabin, and generating, by the carbon dioxide sensor, a fourth output signal. The method includes receiving, by a controller, the first output signal, the second output signal, the third output signal, and the fourth output signal. The method includes selectively processing, by the controller, at least one of the first output signal, the second output signal, the third output signal, or the fourth output signal based on one or more rules. The method further includes controlling, by the controller, the one or more conditions inside the cabin based on the at least one of the first output signal, the second output signal, the third output signal, or the fourth output signal.

In yet another aspect of the present disclosure, a machine is provided. The machine includes a cabin for an operator. The machine comprises an operator presence sensor for detecting presence of an operator inside the cabin, and generating a first output signal. The machine comprises a cabin pressure sensor for determining a pressure inside the cabin, and generating a second output signal. The machine comprises a door sensor for detecting whether doors of the cabin are open, and generating a third output signal. The machine comprises a carbon dioxide sensor for determining a level of carbon dioxide inside the cabin, and generating a fourth output signal. The machine comprises a controller communicably coupled to the operator presence sensor, the cabin pressure sensor, the door sensor, and the carbon dioxide sensor. The controller is configured to receive the first output signal, the second output signal, the third output signal, and the fourth output signal. The controller is configured to selectively process at least one of the first output signal, the second output signal, the third output signal, or the fourth output signal based on one or more rules. The controller is further configured to control the one or more conditions inside the cabin based on the selective processing of the at least one of the first output signal, the second output signal, the third output signal, or the fourth output signal.

DETAILED DESCRIPTION

Wherever possible, the same reference numbers will be used throughout the drawings to refer to same or like parts.

Figure 1:
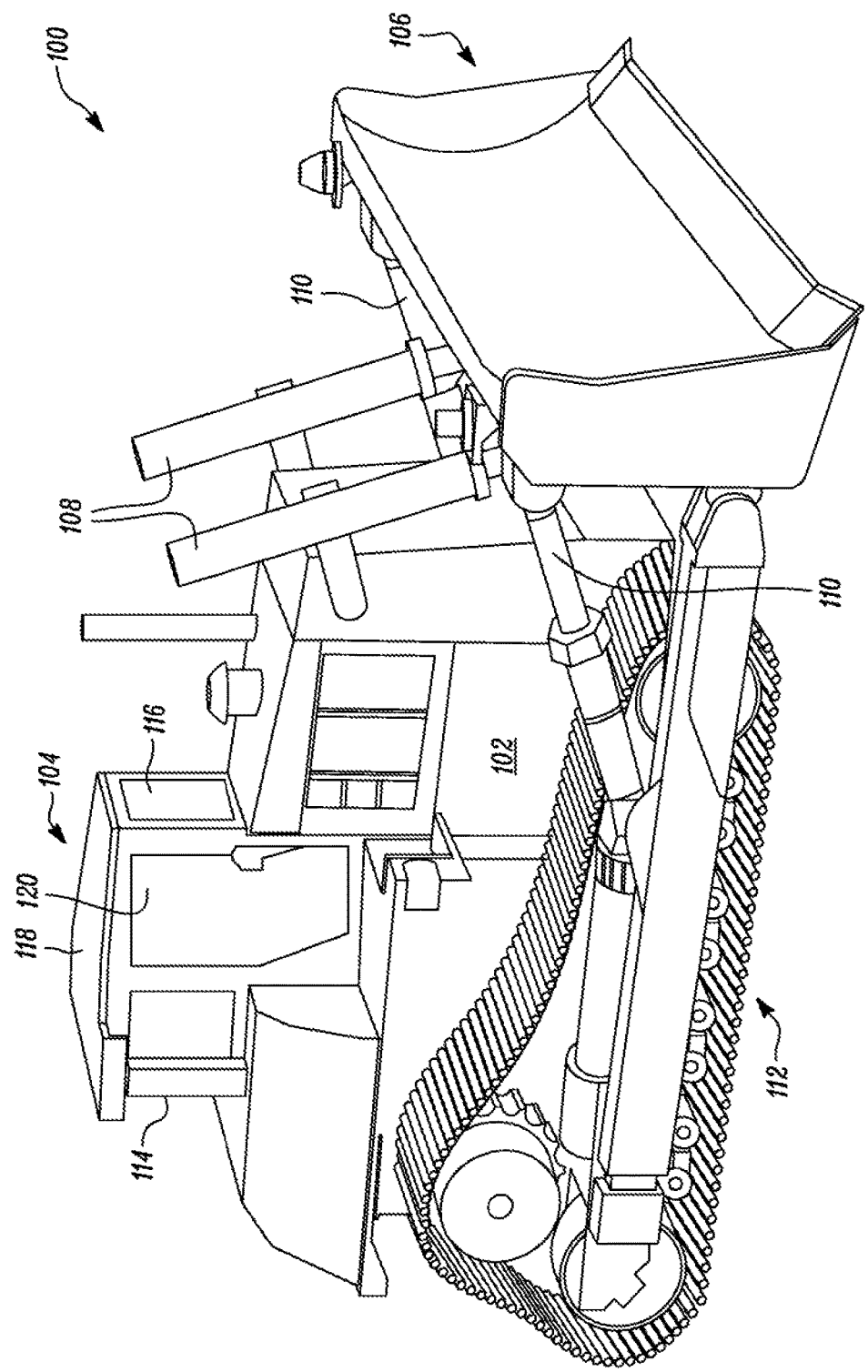
FIG. 1 is a schematic illustration of an exemplary disclosed machine, in accordance with some embodiments of the present disclosure.

FIG. 1 illustrates an exemplary machine 100. The machine 100 may be a mobile machine that performs operations associated with industries such as mining, construction, farming, transportation, landscaping, or the like. For example, the machine 100 may be a track type tractor or dozer (as depicted in FIG. 1), a motor grader, or any other earth-moving machine known in the art. While the following detailed description describes an exemplary aspect in connection with a track type tractor, it should be appreciated that the description applies equally to the use of the present disclosure in other machines.

As shown in FIG. 1, the machine 100 includes a power source 102 and a cabin 104 for an operator. The machine 100 further includes a machine implement 106 (hereinafter interchangeably referred to as an implement 106). Examples of the implement 106 may include a blade or a shovel for moving earth in a worksite. The implement 106 may be moveable by one or more hydraulic mechanisms operatively connected to the cabin 104. The hydraulic mechanisms may include one or more hydraulic lift actuators 108 and one or more hydraulic tilt actuators 110, for moving the implement 106 to various positions, such as, for example, lifting the implement 106 up or lowering the implement 106 down, and tilting the implement 106 left or right. In the illustrated embodiment, the machine 100 includes two hydraulic lift actuators 108 and two hydraulic tilt actuators 110.

The power source 102 may be an engine that provides power to a ground engaging mechanism 112 adapted to support, steer, and propel the machine 100. In some embodiments, the power source 102 may provide power to actuate the hydraulic mechanism to move or position the machine implement 106. The power source 102 may embody an engine such as, for example, a diesel engine, a gasoline engine, a gaseous fuel-powered engine, or any other type of combustion engine known in the art. It is contemplated that the power source 102 may alternatively embody a non-combustion source of power (not shown) such as, for example, a fuel cell, a power storage device, or another suitable source of power. The power source 102 may produce a mechanical or electrical power output that may be converted to hydraulic power for providing power to the ground engaging mechanism 112, the implement 106, the hydraulic lift actuators 108, the hydraulic tilt actuators 110, and other machine components.

The cabin 104 includes a rear wall 114, a front window or wall 116, and a roof 118. The cabin 104 may have one or more doors 120 and one or more windows (not illustrated). The cabin 104 includes an operator's seat (not illustrated), a steering control (also not illustrated) and various other components and equipment for controlling operation of the machine 100. The cabin 104 is configured to provide an operator of the machine 100 with a conducive environment in which to control the machine 100. The cabin 104 may include a user interface (not shown) for operating the machine 100. The user interface may be provided along with or may include, for example, one or more displays. The user interface may be configured to generate commands to propel the machine 100 and/or to control other machine components. The user interface may include one or more joysticks provided within the cabin 104, and adapted to receive an input indicative of a desired movement of the implement 106 from the operator. The display may be configured to convey information or notification to the operator and may include a keyboard, touch screen, or any suitable mechanism for receiving input from the operator to control and/or operate the machine 100, the implement 106, and/or the other machine components.

The machine 100 includes a heating, ventilation, air conditioning (HVAC) unit (not shown) for heating and/or cooling air within the cabin 104 of the machine 100. The HVAC unit includes mechanical arrangements to direct airflow from the inlets to the outlets. An evaporator core is used to reduce the air temperature as air flows through its fins. A heater core is similarly used to increase air temperature as air flows through its fins. An air mix door may be used to vary the blend of hot air (that which has flowed through the heater core) with cold air (that which has flowed through the evaporator core) and is controlled in position by an electrical actuator, servo motor or stepper motor. In some embodiments, the HVAC unit includes a ventilation component configured to supply ambient air inside the cabin 104 to maintain the air quality. A speed of supplying ambient air by the ventilation component may be controlled by a ventilation motor (not shown in FIG. 1).

The machine 100 includes a plurality of sensors (not shown) disposed at various locations inside the cabin 104 for monitoring one or more parameters associated with the cabin 104. The one or more parameters associated with the cabin 104 may include, but not limited to, a pressure, a level of carbon dioxide, a level of particulates, and presence/absence of the operator. In some embodiments, output from some or all of these sensors are integrated to provide a notification to the operator. Further, based on the output of these sensors, one or more conditions inside the cabin 104 are controlled.

Figure 2:
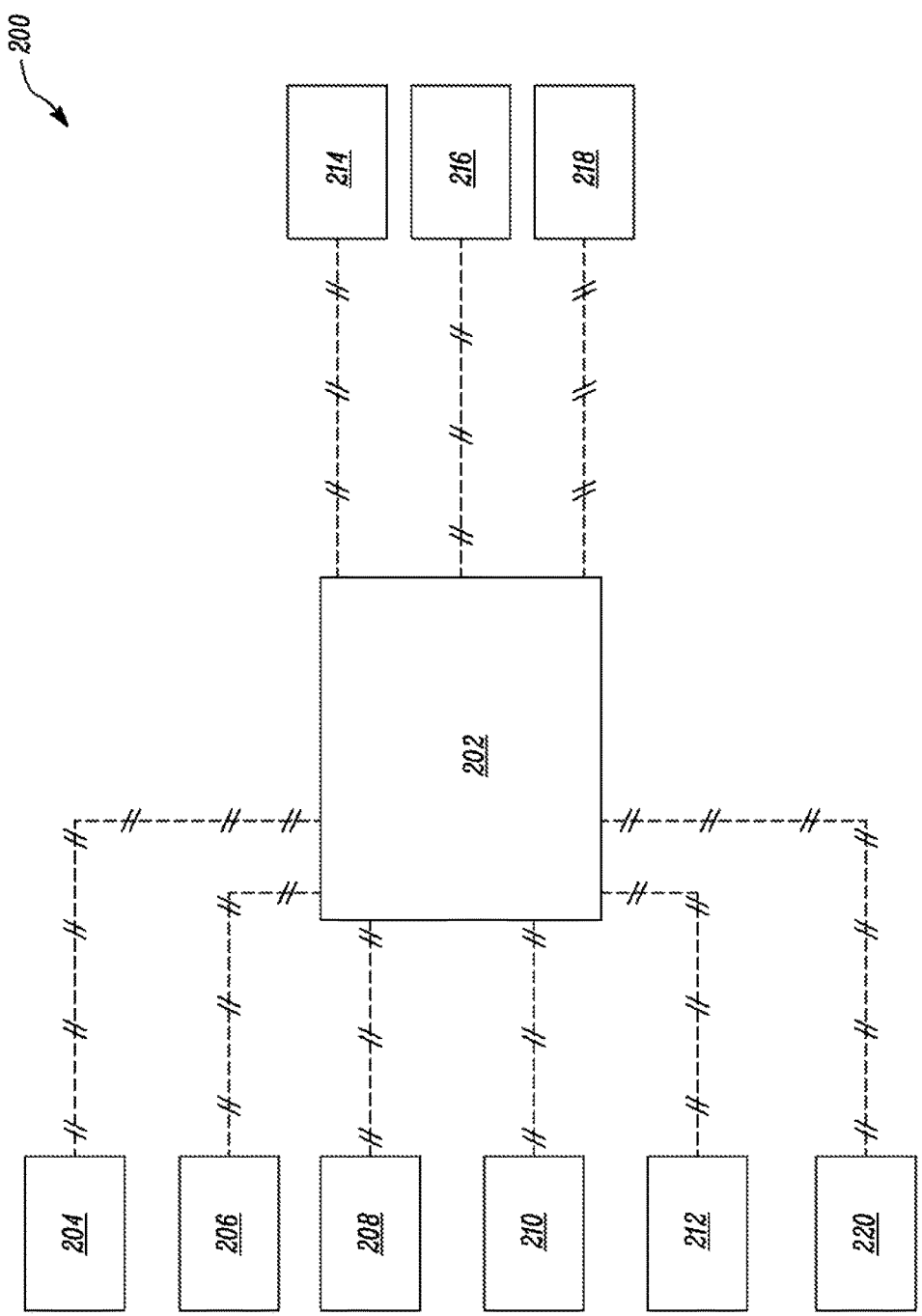
FIG. 2 is a block diagram illustrating a system for controlling one or more conditions inside the cabin, in accordance with some embodiments of the present disclosure.

FIG. 2 is a block diagram illustrating a system 200 to control one or more conditions inside the cabin 104, in some embodiments of the present invention. The system 200 includes a controller 202 configured to control the air quality. The system 200 includes an operator presence sensor 204, a cabin pressure sensor 206, a door sensor 208, a carbon dioxide sensor 210, and a window sensor 212. The controller 202 is communicably coupled to the operator presence sensor 204, the cabin pressure sensor 206, the door sensor 208, the carbon dioxide sensor 210, and the window sensor 212. The operator presence sensor 204, the cabin pressure sensor 206, the door sensor 208, the carbon dioxide sensor 210, and the window sensor 212 are configured to output a first output signal, a second output signal, a third output signal, a fourth output signal, and a fifth output signal, respectively. In some embodiments, the system 200 includes a particulate sensor 220 to determine a level of particulates inside the cabin 104. The particulate sensor 220 may be configured to generate a sixth output signal indicating the level of particulates inside the cabin 104.

When the machine 100 is powered on, the system 200 starts the monitoring of the cabin 104 by detecting whether the operator is present inside the cabin 104 or not. Referring to FIG. 2, the system 200 includes the operator presence sensor 204 for detecting presence of the operator inside the cabin 104. The operator presence sensor 204 is configured to generate the first output signal. The first output signal provides an indication of whether the operator is present or not present in the cabin 104. In some embodiments, when the first output signal indicates that the operator is not present in the cabin 104, the controller 202 may generate a first notification indicating that the operator is not present in the cabin 104. The controller 202 may generate an analytics report including the first notification. The controller 202 may be configured to communicate (or transmit) the analytics report via a wired or a wireless network to one or more devices associated with a user (e.g., an operator of the machine 100, a site personnel, a service technician, etc.) or a remote back office. In some embodiments, the one or more devices may be located in a location remote from the machine 100 (e.g., a remote back office). Additionally, or alternatively, the one or more devices may include a mobile device (of a user) to keep track of the operational state of the machine 100. In another embodiment, recipient of the analytics report may be the operator of the machine 100, who may be prompted to take appropriate control actions accordingly. The controller 202 may communicate the analytics report to any other device or system configured to control the air quality inside the cabin 104. The first notification may indicate that the operator is not present inside the cabin 104 while the machine 100 is powered on. Upon receiving the analytics report, one or more follow-up actions such as calling the operator or a site manager may be performed by the recipient of the analytics report based on the first notification. In some embodiments, the one or more devices receiving the analytics report may cause the one or more follow-up actions to be performed. Thus, the controller 202 helps in ensuring safety of the machine 100 and site staff using the first notification.

After detecting that the operator is present inside the cabin 104, the controller 202 checks whether the cabin pressure is within an operating range of cabin pressure. The controller 202 processes the second output signal from the cabin pressure sensor 206. The cabin pressure sensor 206 is configured to determine a pressure inside the cabin 104, either continuously or at distinct intervals and generate the second output signal. The controller 202 may be configured to store a first threshold of cabin pressure and a second threshold of cabin pressure (the second threshold exceeding the first threshold). The controller 202 is configured to detect whether the pressure indicated by the second output signal is lower than the first threshold of cabin pressure.

Upon detecting that the cabin pressure is lower than the first threshold, the controller 202 processes the third output signal from the door sensor 208 in order to investigate probable causes for the low pressure inside the cabin 104. The door sensor 208 is configured to detect whether doors 120 of the cabin 104 are open and generate the third output signal. In case, the third output signal indicates that doors 120 of the cabin 104 are open, the controller 202 is configured to control the pressure inside the cabin 104 by automatically closing doors 120 of the cabin 104. Electrical actuators, servo motors and stepper motors may be used for automatically closing the doors 120. Referring to FIG. 2, the controller 202 may be configured to control a door motor 214 to close doors 120 of the cabin 104. In some embodiments, the controller 202 may also generate a second notification indicating that the doors 120 of the cabin 104 are open. The second notification may be an alarm, a LED light, or any other indication that may be provided to the operator. The controller 202 may include the second notification in the analytics report. Upon receiving the analytics report, one or more corrective actions such as checking the doors 120 for any fault or scheduling maintenance of the doors 120 may be performed by the recipient of the analytics report based on the second notification. In some embodiments, the one or more devices receiving the analytics report may schedule the maintenance of the doors automatically upon receiving the analytics report. In other words, the controller 202 may cause the one or more devices to schedule the maintenance of the doors. Thus, the controller 202 helps in maintaining the pressure inside the cabin 104 using the second notification.

In case the third output signal indicates that doors 120 of the cabin 104 are closed, the controller 202, in some embodiments, may be configured to detect whether one or more windows of the cabin 104 are open. The system 200 includes the window sensor 212 configured to detect whether one or more windows of the cabin 104 are open and generate the fifth output signal. In case, the fifth output signal indicates that windows of the cabin 104 are open, the controller 202 may be configured to control the pressure inside the cabin 104 by automatically closing the one or more windows of the cabin 104. Electrical actuators, servo motors and stepper motors may be used for automatically closing the one or more windows. Referring to FIG. 2, the controller 202 may be configured to control a window motor 216 to close the one or more windows of the cabin 104.

When the controller 202 detects that the pressure inside the cabin 104 is adequate i.e. between the first threshold of cabin pressure and the second threshold of cabin pressure, the controller 202 proceeds on to check a level of carbon dioxide inside the cabin 104. Still referring to FIG. 2, the system 200 includes the carbon dioxide sensor 210 for determining the level of carbon dioxide inside the cabin 104. The carbon dioxide sensor 210 is configured to generate the fourth output signal indicating the level of carbon dioxide inside the cabin 104. The controller 202 may be configured to store a third threshold of carbon dioxide level representing threshold allowable level of carbon dioxide (e.g., a maximum allowable level of carbon dioxide). The controller 202 may be configured to determine whether the level of carbon dioxide inside the cabin 104 is more than the third threshold of carbon dioxide level.

Upon determining that that the level of carbon dioxide is more than the third threshold of carbon dioxide levels, the controller 202 is configured to increase a speed of the ventilation component of the HVAC unit to introduce more ambient air inside the cabin 104. This results in a reduction in the carbon dioxide level inside the cabin 104 and improvement in air quality inside the cabin 104. Referring to FIG. 2, the system 200 includes a ventilation motor 218 to control a speed of supplying ambient air by the ventilation component. In some embodiments, upon determining that the level of carbon dioxide is less than the third threshold of carbon dioxide level, the controller 202 may proceed on to checking the level of particulates inside the cabin 104 based on the sixth output signal generated by the particulate sensor 220. The particulate sensor 220 generates the sixth output signal indicating the level of particulates inside the cabin 104. The controller 202 receives the sixth output signal from the particulate sensor 220. Further, the controller 202 may be configured to store a threshold level of particulates and determine whether the level of particulates measured by the particulate sensor 220 inside the cabin 104 is more than the threshold level of particulates. If yes, the controller 202 may generate a third notification for the operator indicating that a recirculation filter needs to be replaced. The controller 202 may include the third notification in the analytics report. Upon receiving the analytics report, one or more corrective actions such as replacing the recirculation filter, scheduling maintenance of the recirculation filter may be performed by the recipient of the analytics report based on the third notification. In some embodiments, the one or more devices receiving the analytics report may schedule the maintenance of the recirculation filter automatically upon receiving the analytics report. In other words, the controller 202 may cause the one or more devices to schedule the maintenance of the recirculation filter. Thus, the controller 202 may help in maintaining the level of particulates inside the cabin 104.

The controller 202 is configured to receive the first output signal, the second output signal, the third output signal, the fourth output signal, and the fifth output signal. The controller 202 is configured to selectively process at least one of the first output signal, the second output signal, the third output signal, the fourth output signal, or the fifth output signal based on one or more rules. The one or more rules may be designed to carry out sequential processing of some or all of the received output signals by the controller 202. For example, the controller 202 processes the third output signal from the door sensor 208 only if the second output signal from the cabin pressure sensor 206 indicates that the cabin pressure is outside an operating range of the cabin pressure. In some embodiments, a program that can be run by the controller 202 to perform one or more control algorithms that are consistent with the teachings of the present invention may be stored in a memory and can be accessed via bus.

The controller 202 is configured to control one or more conditions inside the cabin 104 based on at least one of the first output signal, the second output signal, the third output signal, the fourth output signal, or the fifth output signal. The one or more conditions include a pressure inside the cabin 104, a level of air quality, and/or a level of carbon dioxide inside the cabin 104. In some embodiments, the controller 202 is configured to control the pressure inside the cabin 104 by automatically closing doors 120 of the cabin 104. The controller 202 may be configured to control the door motor 214 to close doors 120 of the cabin 104. Additionally, or alternatively, the controller 202 may be configured to control the pressure inside the cabin 104 by automatically closing windows of the cabin 104. The controller 202 may be configured to control the window motor 216 to close windows of the cabin 104. In some embodiments, the controller 202 may be configured to control the level of carbon dioxide by increasing the speed of the ventilation component of the HVAC unit to introduce ambient air inside the cabin 104.

INDUSTRIAL APPLICABILITY

The present disclosure is related to a method and a system for monitoring the cabin 104 of the machine 100. The exemplary disclosed controller 202 may be applicable to any cabin 104 to process output of the operator presence sensor 204, the cabin pressure sensor 206, the door sensor 208, and the carbon dioxide sensor 210 and identifies any abnormality in the cabin conditions. Further, the controller 202 is configured to control one or more conditions of the cabin 104 based on the processing of the at least one of the first output signal, the second output signal, the third output signal or the fourth output signal. In this way, output signals from the different sensors are integrated by the controller 202 to help the operator and service technicians in maintaining cabin air quality.

Figure 3:
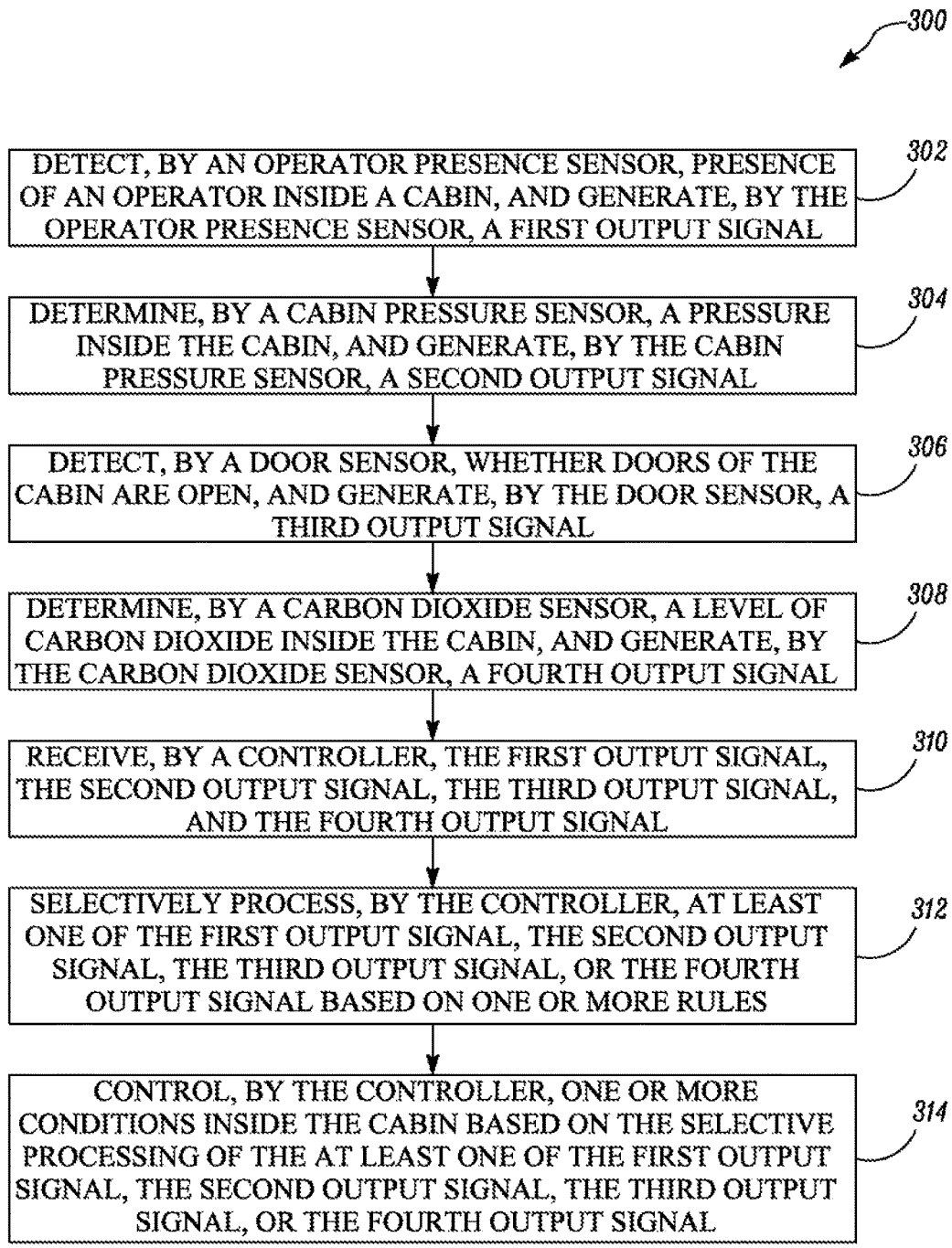
FIG. 3 is a flowchart of a method for controlling the one or more conditions inside the cabin, in accordance with some embodiments of the present disclosure.

Referring to FIG. 3, a method 300 of controlling one or more conditions inside the cabin 104 of the machine 100 is illustrated. At step 302, the operator presence sensor 204 detects the presence of the operator inside the cabin 104 of the machine 100 and generates the first output signal. At step 304, the cabin pressure sensor 206 determines the pressure inside the cabin 104 and generates the second output signal. At step 306, the door sensor 208 detects whether doors 120 of the cabin 104 are open and generates the third output signal. Additionally, the window sensor 212 may be provided to detect whether one or more windows of the cabin 104 are open and accordingly generate the fifth output signal indicating whether one or more windows of the cabin 104 are open. At step 308, the carbon dioxide sensor 210 determines the level of carbon dioxide inside the cabin 104 and generates the fourth output signal.

At step 310, the controller 202 is configured to receive the first output signal, the second output signal, the third output signal and the fourth output signal. In some embodiments, the controller 202 may also receive the fifth output signal. At step 312, the controller 202 is configured to selectively process at least one of the first output signal, the second output signal, the third output signal or the fourth output signal based on the one or more rules. The controller 202 may be configured to determine whether at least one of the first output signal, the second output signal, the third output signal or the fourth output signal falls within a respective operating range. In some embodiments, the controller 202 may also process the fifth output signal based on the one or more rules. At step 314, the controller 202 is configured to control the one or more conditions inside the cabin 104 based on the at least one of the first output signal, the second output signal, the third output signal or the fourth output signal.

The method 300 further includes detecting whether one or more windows of the cabin 104 are open by the window sensor 212, and generating the fifth output signal indicating whether one or more windows of the cabin 104 are open. The method 300 includes receiving the fifth output signal by the controller 202, and determining whether the one or more windows of the cabin 104 are open based on the fifth output signal. The method 300 includes automatically closing the one or more windows of the cabin 104 when the fifth output signal from the window sensor 212 indicates that the one or more windows of the cabin 104 are open.

The method 300 further includes selectively processing the second output signal indicative of the pressure inside the cabin 104 from the cabin pressure sensor 206 by the controller 202 to determine whether the pressure inside the cabin 104 is less than the first threshold of cabin pressure, upon detecting that the operator is present inside the cabin 104. The method 300 includes controlling the pressure inside the cabin 104 based by the controller 202 based on the determination that the pressure inside the cabin 104 is less than the first threshold of cabin pressure.

The method 300 further includes selectively processing the third output signal indicative of whether doors 120 of the cabin 104 are open from the door sensor 208 by the controller 202 to determine whether doors 120 of the cabin 104 are open, upon determining that the pressure inside the cabin 104 is less than the first threshold of cabin pressure. The method 300 includes automatically closing the doors 120 of the cabin 104 by the controller 202 to maintain the cabin pressure upon determining that doors 120 of the cabin 104 are open.

The method 300 further includes selectively processing the fourth output signal indicative of the level of carbon dioxide from the carbon dioxide sensor 210 by the controller 202 to determine that the level of carbon dioxide is more than the third threshold of carbon dioxide level, upon determining that the pressure inside the cabin 104 is less than the second threshold of cabin pressure but more than the first threshold of cabin pressure. The method 300 includes increasing the speed of the ventilation component to introduce more ambient air inside the cabin 104 by the controller 202 to reduce the level of carbon dioxide in the cabin 104, based on determining that the level of carbon dioxide is more than the third threshold of carbon dioxide level. In this regard, controlling the one or more conditions may include increasing the speed of the ventilation component to introduce more ambient air inside the cabin 104, or automatically closing doors 120 of the cabin 104 based on the selective processing of the at least one of the first output signal, the second output signal, the third output signal, or the fourth output signal.

While aspects of the present disclosure have been particularly shown and described with reference to the embodiments above, it will be understood by those skilled in the art that various additional embodiments may be contemplated by the modification of the disclosed machines, systems and methods without departing from the spirit and scope of what is disclosed. Such embodiments should be understood to fall within the scope of the present disclosure as determined based upon the claims and any equivalents thereof.

What is claimed is:

1. A system for controlling one or more conditions inside a cabin of a machine, the system comprising:
    an operator presence sensor for detecting presence of an operator inside the cabin, and generate a first output signal;
    a cabin pressure sensor for determining a pressure inside the cabin, and generate a second output signal;
    a door sensor for detecting whether doors of the cabin are open, and generate a third output signal;
    a carbon dioxide sensor for determining a level of carbon dioxide inside the cabin, and generate a fourth output signal; and
    a controller communicably coupled to the operator presence sensor, the cabin pressure sensor, the door sensor, and the carbon dioxide sensor, wherein the controller is configured to:
        receive the first output signal, the second output signal, the third output signal, and the fourth output signal;
        selectively process at least one of the first output signal, the second output signal, the third output signal, or the fourth output signal based on one or more rules; and
        control the one or more conditions inside the cabin based on the selective processing of the at least one of the first output signal, the second output signal, the third output signal, or the fourth output signal.

2. The system of claim 1 further comprising a window sensor to detect whether one or more windows of the cabin are open and generate a fifth output signal, wherein the controller is configured to receive the fifth output signal and determine whether the one or more windows of the cabin are open based on the fifth output signal.

3. The system of claim 2, wherein, when controlling the one or more conditions, the controller is configured to control the pressure inside the cabin by automatically closing the one or more windows of the cabin when the fifth output signal from the window sensor indicates that the one or more windows of the cabin are open.

4. The system of claim 1, wherein the controller is configured to:
    detect that the operator is present inside the cabin based on the first output signal; and
    process the second output signal from the cabin pressure sensor to determine whether the pressure inside the cabin is less than a first threshold of cabin pressure upon detecting that the operator is present inside the cabin.

5. The system of claim 4, wherein the controller is configured to:
    determine that the pressure inside the cabin is less than a first threshold of cabin pressure based on the second output signal from the cabin pressure sensor;
    process the third output signal from the door sensor to determine whether doors of the cabin are open upon determining that the pressure inside the cabin is less than the first threshold of cabin pressure; and
    automatically close the doors of the cabin to maintain the cabin pressure upon determining that doors of the cabin are open.

6. The system of claim 1, wherein the controller is configured to:
    determine that the pressure inside the cabin is less than a second threshold of cabin pressure but more than a first threshold of cabin pressure, wherein the second threshold exceeds the first threshold; and
    process the fourth output signal from the carbon dioxide sensor to determine that the level of carbon dioxide is more than a third threshold of carbon dioxide level upon determining that the pressure inside the cabin is less than the second threshold of cabin pressure but more than the first threshold of cabin pressure.

7. The system of claim 6, wherein, when controlling the one or more conditions, the controller is configured to:
    process the fourth output signal from the carbon dioxide sensor and determining that the level of carbon dioxide is more than a third threshold of carbon dioxide level; and
    increase a speed of a ventilation component to introduce more ambient air inside the cabin to reduce a level of carbon dioxide in the cabin.

8. The system of claim 1, wherein, when controlling the one or more conditions, the controller is configured to control the pressure inside the cabin by automatically closing doors of the cabin when the third output signal from the door sensor indicates that doors of the cabin are open.

9. A method for controlling one or more conditions inside a cabin of a machine, the method comprising:
    detecting, by an operator presence sensor, presence of an operator inside the cabin, and generating, by the operator presence sensor, a first output signal;
    determining, by a cabin pressure sensor, a pressure inside the cabin, and generating, by the cabin pressure sensor, a second output signal;
    detecting, by a door sensor, whether doors of the cabin are open, and generating, by the door sensor, a third output signal;
    determining, by a carbon dioxide sensor, a level of carbon dioxide inside the cabin, and generating, by the carbon dioxide sensor, a fourth output signal;
    receiving, by a controller, the first output signal, the second output signal, the third output signal, and the fourth output signal;
    selectively processing, by the controller, at least one of the first output signal, the second output signal, the third output signal, or the fourth output signal based on one or more rules; and
    controlling, by the controller, the one or more conditions inside the cabin based on the selective processing of the at least one of the first output signal, the second output signal, the third output signal, or the fourth output signal.

10. The method of claim 9 further comprising:
    detecting, by a window sensor, whether one or more windows of the cabin are open;
    generating a fifth output signal based on the detection whether the one or more windows of the cabin are open;
    receiving, by the controller, the fifth output signal;
    determining whether the one or more windows of the cabin are open based on the fifth output signal; and automatically closing the one or more windows of the cabin when the fifth output signal from the window sensor indicates that the one or more windows of the cabin are open.

11. The method of claim 9, further comprising:
selectively processing, by the controller, the second output signal from the cabin pressure sensor to determine whether the pressure inside the cabin is less than a first threshold of cabin pressure upon detecting that the operator is present inside the cabin; and
controlling, by the controller, the pressure inside the cabin based on the determination that the pressure inside the cabin is less than the first threshold of cabin pressure.

12. The method of claim 9, further comprising:
selectively processing, by the controller, the third output signal from the door sensor to determine whether doors of the cabin are open upon determining that the pressure inside the cabin is less than a first threshold of cabin pressure; and
automatically closing, by the controller, the doors of the cabin to maintain the cabin pressure upon determining that doors of the cabin are open.

13. The method of claim 9, further comprising:
selectively processing, by the controller, the fourth output signal from the carbon dioxide sensor to determine that the level of carbon dioxide is more than a third threshold of carbon dioxide level upon determining that the pressure inside the cabin is less than the second threshold of cabin pressure but more than the first threshold of cabin pressure; and
increasing, by the controller, a speed of a ventilation component to introduce more ambient air inside the cabin to reduce the level of carbon dioxide in the cabin.

14. The method of claim 9, wherein controlling the one or more conditions includes at least one of increasing a speed of a ventilation component to introduce more ambient air inside the cabin or automatically closing doors of the cabin based on the selective processing of the at least one of the first output signal, the second output signal, the third output signal, or the fourth output signal.

15. A machine comprising:
a cabin for an operator;
an operator presence sensor for detecting presence of the operator inside the cabin, and generating a first output signal;
a cabin pressure sensor for determining a pressure inside the cabin, and generating a second output signal;
a door sensor for detecting whether doors of the cabin are open, and generating a third output signal;
a carbon dioxide sensor for determining a level of carbon dioxide inside the cabin, and generating a fourth output signal; and
a controller communicably coupled to the operator presence sensor, the cabin pressure sensor, the door sensor, and the carbon dioxide sensor, wherein the controller is configured to:
receive the first output signal, the second output signal, the third output signal, and the fourth output signal;
selectively process at least one of the first output signal, the second output signal, the third output signal, or the fourth output signal based on one or more rules; and
control the one or more conditions inside the cabin based on the selective processing of the at least one of the first output signal, the second output signal, the third output signal, or the fourth output signal.

16. The machine of claim 15 further comprising a window sensor to detect whether one or more windows of the cabin are open and generate a fifth output signal, wherein the controller is configured to receive the fifth output signal and determine whether the one or more windows of the cabin are open based on the fifth output signal, and automatically close the one or more windows of the cabin when the fifth output signal from the window sensor indicates that the one or more windows of the cabin are open.

17. The machine of claim 16, wherein, when controlling the one or more conditions, the controller is configured to control the pressure inside the cabin by automatically closing the one or more windows of the cabin when the fifth output signal from the window sensor indicates that the one or more windows of the cabin are open.

18. The machine of claim 15, wherein, when controlling the one or more conditions, the controller is configured to:
process the fourth output signal from the carbon dioxide sensor and determining that the level of carbon dioxide is more than a third threshold of carbon dioxide level; and
increase a speed of a ventilation component to introduce more ambient air inside the cabin to reduce the level of carbon dioxide in the cabin.

19. The machine of claim 15, wherein, when controlling the one or more conditions, the controller is configured to control the pressure inside the cabin by automatically closing doors of the cabin when the third output signal from the door sensor indicates that doors of the cabin are open.

20. The machine of claim 15, wherein the controller is configured to detect that the operator is present inside the cabin based on the first output signal and process the second output signal from the cabin pressure sensor to determine whether the pressure inside the cabin is less than a first threshold of cabin pressure upon detecting that the operator is present inside the cabin, and control the pressure inside the cabin based on the determination that the pressure inside the cabin is less than the first threshold of cabin pressure.

* * * * *